(12) United States Patent
Fulton (10) Patent No.: US 9,861,385 B2
(45) Date of Patent: Jan. 9, 2018

(54) SURGICAL NEEDLE WITH ENHANCED ULTRASOUND REFLECTIVITY

(71) Applicant: NFINIUM VASCULAR TECHNOLOGIES, LLC, Grand Junction, CO (US)

(72) Inventor: Richard Eustis Fulton, Grand Junction, CO (US)

(73) Assignee: NFINIUM VASCULAR TECHNOLOGIES, LLC, Grand Junction, CO (US)

( * ) Notice: Subject to any disclaimer, the term of this patent is extended or adjusted under 35 U.S.C. 154(b) by 0 days.

(21) Appl. No.: 15/065,950

(22) Filed: Mar. 10, 2016

(65) Prior Publication Data
US 2016/0183924 A1 Jun. 30, 2016

Related U.S. Application Data

(66) Division of application No. 13/828,964, filed on Mar. 14, 2013, Substitute for application No. 61/685,390, filed on Mar. 16, 2012.
(Continued)

(51) Int. Cl.
*A61B 18/14* (2006.01)
*A61B 17/34* (2006.01)
(Continued)

(52) U.S. Cl.
CPC .......... *A61B 17/3403* (2013.01); *A61B 8/481* (2013.01); *A61B 18/18* (2013.01);
(Continued)

(58) Field of Classification Search
CPC ........ A61B 17/3403; A61B 2017/3413; A61B 2019/5425; A61B 2019/5429; A61B 2090/3925; A61B 90/39; A61M 25/0108
(Continued)

(56) References Cited

U.S. PATENT DOCUMENTS 4,055,167 A 10/1977 Bernstein
4,207,901 A 6/1980 Nigam
(Continued)

OTHER PUBLICATIONS

Notice of Allowance dated Jul. 7, 2016 for U.S. Appl. No. 13/828,964.
(Continued)

*Primary Examiner* — Jaymi Della
(74) *Attorney, Agent, or Firm* — Wilson Sonsini Goodrich & Rosati (57) ABSTRACT

A surgical needle having notches in a sidewall with enhanced ultrasound reflectivity is disclosed. Indentations, ridges, projections, overhanging edges, and other structures are formed in the notches to retain small amounts of air or other reflective material as the surgical needle is passed through tissue. The additional amounts of reflective material retained by these structures will significantly enhance the ultrasound reflectivity and enhance the response to ultrasonic probing to provide an enhanced image during needle placement in a medical patient so that the needle may be accurately placed as desired. Alternatively or additionally, the notches are filled with a substance that contains air bubbles suspended in the substance wherein the suspended air bubbles provide the reflectivity enhancement. In both embodiments, the needle will be visible at any angle in which the device is used in a medical patient.

14 Claims, 7 Drawing Sheets

Related U.S. Application Data (60) Provisional application No. 61/686,694, filed on Apr. 10, 2012.

(51) Int. Cl.
  *A61B 18/18* (2006.01)
  *A61B 8/08* (2006.01)
  *A61M 25/01* (2006.01)
  *A61B 90/00* (2016.01)

(52) U.S. Cl.
  CPC .............. *A61B 2017/3413* (2013.01); *A61B 2090/3925* (2016.02); *A61M 25/0108* (2013.01)

(58) Field of Classification Search
  USPC ............... 600/407, 437, 458, 461, 463–464; 604/264, 272, 411–412, 6.05–606; 606/185, 44
  See application file for complete search history.

(56) References Cited

U.S. PATENT DOCUMENTS

| | | | |
|---|---|---|---|
| 4,401,124 A | 8/1983 | Guess et al. | |
| 4,566,438 A | 1/1986 | Liese et al. | |
| 4,582,061 A | 4/1986 | Fry | |
| 4,627,444 A | 12/1986 | Brooker | |
| 4,702,260 A | 10/1987 | Wang | |
| 4,791,937 A | 12/1988 | Wang | |
| 4,799,495 A | 1/1989 | Hawkins et al. | |
| 4,869,259 A | 9/1989 | Elkins | |
| 4,900,300 A | 2/1990 | Lee | |
| 4,903,709 A | 2/1990 | Skinner | |
| 4,977,897 A | 12/1990 | Hurwitz | |
| 4,986,279 A | 1/1991 | O'Neill | |
| 4,989,614 A | 2/1991 | Dejter, Jr. et al. | |
| 4,991,592 A | 2/1991 | Christ | |
| 5,048,530 A | 9/1991 | Hurwitz | |
| 5,081,997 A | 1/1992 | Bosley, Jr. et al. | |
| 5,106,364 A | 4/1992 | Hayafuji et al. | |
| 5,213,569 A | 5/1993 | Davis | |
| 5,221,269 A | 6/1993 | Miller et al. | |
| 5,320,110 A | 6/1994 | Wang | |
| 5,383,466 A | 1/1995 | Partika | |
| 5,402,792 A | 4/1995 | Kimura | |
| 5,449,001 A | 9/1995 | Terwilliger | |
| 5,458,112 A | 10/1995 | Weaver | |
| 5,470,308 A | 11/1995 | Edwards et al. | |
| 5,490,521 A | 2/1996 | Davis et al. | |
| 5,611,345 A | 3/1997 | Hibbeln | |
| 5,766,135 A | 6/1998 | Terwilliger | |
| 5,769,795 A | 6/1998 | Terwilliger | |
| 5,795,311 A | 8/1998 | Wess | |
| 5,807,304 A | 9/1998 | Cockburn | |
| 5,817,033 A | 10/1998 | DeSantis et al. | |
| 5,865,765 A | 2/1999 | Mohajer | |
| 5,971,939 A | 10/1999 | DeSantis et al. | |
| 6,053,870 A * | 4/2000 | Fulton, III | A61B 17/3421 600/458 |
| 6,709,408 B2 | 3/2004 | Fisher | |
| 9,445,837 B2 | 9/2016 | Fulton, III | |
| 2004/0106891 A1 | 6/2004 | Langan et al. | |
| 2004/0249288 A1 | 12/2004 | Ichikawa | |
| 2009/0054773 A1 | 2/2009 | Shizuka | |
| 2009/0118641 A1 | 5/2009 | Van Dam et al. | |
| 2012/0253228 A1 | 10/2012 | Schembre et al. | |
| 2014/0265024 A1* | 9/2014 | Quearry | A61B 8/4455 264/293 |

OTHER PUBLICATIONS

Notice of Allowance dated Jul. 18, 2016 for U.S. Appl. No. 13/828,964.
Office Action dated Jan. 11, 2016 for U.S. Appl. No. 13/828,964.
Office Action dated Mar. 10, 2015 for U.S. Appl. No. 13/828,964.
Office Action dated Mar. 17, 2014 for U.S. Appl. No. 13/828,964.
Office Action dated Aug. 14, 2014 for U.S. Appl. No. 13/828,964.
Office Action dated Oct. 21, 2015 for U.S. Appl. No. 13/828,964.
Office Action dated Nov. 25, 2014 for U.S. Appl. No. 13/828,964.

* cited by examiner

SURGICAL NEEDLE WITH ENHANCED ULTRASOUND REFLECTIVITY

CROSS-REFERENCE TO RELATED APPLICATION

This application is a divisional of U.S. application Ser. No. 13/828,964, filed Mar. 14, 2013, which claims the benefit of U.S. provisional patent Application No. 61/685,390 filed Mar. 16, 2012 entitled "Surgical Needle with Enhanced Ultrasound Reflectivity", and U.S. provisional Patent Application No. 61/686,694 filed Apr. 10, 2012 entitled "Surgical Needle with Added Ultrasound Reflectivity", the disclosures of which are hereby incorporated by reference.

BACKGROUND

This invention relates to a medical device that provides enhanced image and response to an ultrasound signal and more particularly to a surgical needle having geometric features that provides an enhanced image and response.

Ultrasonic imaging has long been used in medical practice to provide images not only of body organs and parts but also of the medical instruments and in particular needles that are used in connection with various medical procedures.

For example, ultrasonic imaging is used to guide a medical needle into a body part to effect a biopsy, to inject material or liquids, to access fluid collection for sampling or drainage, to obtain vascular access and to access the urinary and biliary tracts. Ultrasonic imaging is also used to place a needle at a tumor or other body structure for subsequent surgical removal or to ablate the tumor with a variety of energies or methods.

A major limitation on the ultrasonic guided intervention or procedures are the inability to image the medical instrument or needle adequately in many circumstances. The visibility of the needle is strongly dependent on the particular geometrical relationship between the transducer that provides the ultrasonic beam and the reflective surface of the instrument. The amount of ultrasonic energy reflected from the instrument toward the transducer (an ultrasonic echo sensor) determines the quality of the image of the instrument on the monitor. If the needle is in the plane of the interrogating ultrasonic beam and horizontal to the face of the sensing transducer, or perpendicular to the direction of the incident beam, the reflected energy is optimized and a usable visible image is obtained. However, as the needle becomes less perpendicular to the direction of the incident beam, lesser amounts of ultrasonic energy are reflected to the sensor and the instrument is imaged poorly or not at all.

The optimal geometric relationship is difficult to maintain in all but fairly limited applications of ultrasonic guided interventions. It becomes nearly impossible to maintain the optimum geometry in many instances because of intervening organs or structures. This results in poor visualization of the instrument, procedure time is lengthened and complexities are created which would not be present if the needle were easily seen.

Multiple passes with a needle may have to be made before it can be visualized causing tissue damage within adjacent organs or structures and creating the potential of bleeding and other complications. There are times when the physician is able to visualize the target lesion quite well but not the needle or other instrument. Moving the sensing transducer can result in the needle being imaged but the image of the target lesion is lost. A series of trial and error maneuvers are employed. Breathing motion of the patient further complicates the process.

This problem has been addressed by a large number of proposed designs, including those shown in U.S. Pat. No. 4,869,259, U.S. Pat. No. 4,977,897, U.S. Pat. No. 5,048,530, U.S. Pat. No. 5,081,997, U.S. Pat. No. 5,213,569, U.S. Pat. No. 5,221,269, U.S. Pat. No. 5,383,466, U.S. Pat. No. 5,490,521, U.S. Pat. No. 5,611,345, U.S. Pat. No. 5,766,135 and U.S. Pat. No. 5,769,795. The problem has also been addressed in the inventor's U.S. Pat. No. 6,053,870 which is incorporated herein by reference, and which is a definite improvement over other prior art devices.

The devices shown in the above referenced patents are intended to enhance ultrasonic visibility. Some of these devices are complex and expensive to manufacture. Some of these devices are difficult to manipulate within the patient such as the square rectangular shaped needle suggested in U.S. Pat. No. 5,611,345. Furthermore, many of the devices only marginally enhance ultrasonic visibility.

SUMMARY

In brief, one embodiment of this invention is a surgical needle manufactured of stainless steel or some other material which provides an interface with human tissue that results in an ultrasonic echo. One or more notches are created in the sidewall of the needle. The notch may be a wedge-shaped, triangular, multifaceted, trihedral or other shaped notch defining at least a first and second walls in the sidewall of the lumen. Where these walls are planar, the plane of each wall intersects the axis of the needle at an acute, obtuse or right angle. The walls created by the notch provide a large amount of reflective surface area. Additional indentations or ridges within the notch will enhance the reflectivity and create additional air containing pockets or sites within these notches to enhance reflectivity even more.

In another embodiment, the needle may be solid or the needle may have a lumen and the notches may or may not extend into the lumen. The notches may be only on one side so as to preserve a smooth side to delivery electrical current, heat, cold, radiofrequency, irreversible electroporation, and the like uniformly to select tissue or tumors, or the notches may be only on one side for other reasons including limiting the reflectivity.

In operation, when an embodiment of a needle is inserted into a patient, the surface of the needle will reflect incident ultrasonic energy in directions that are determined by the needle sidewall and the notch walls. The result is to reflect ultrasonic energy at a substantial range of angles. When the needle is inserted into a patient, sufficient amount of air is entrained so as to provide small air, $CO_2$, microspheres, contrast agent, etc., bubbles which form on or are trapped in the notches. These air bubbles provide a further sound velocity contrast with tissue so as to enhance wide angle reflection of an incident ultrasonic energy pulse. In this fashion, the ultrasonic echo sensor can have a wide variety of spatial orientations relative to the needle and yet receive a strong enough ultrasonic echo to provide a usable and useful image of the needle. Alternatively, air, $CO_2$, microspheres, contrast agent, amongst other materials may be purposefully placed within the notches or applied to the notches in one of several methods to enhance the visibility of the notches. Doing so acts to enhance or promote the entrainment and retention of these additional reflective surfaces within the notches.

While the notches may be triangular, transverse, oval, multifaceted, or any other shape, the construction of the notches is important in other respects. A notch that is able to retain small amounts of air while the shaft traverses tissue will simply reflect better than a notch that is not able to retain the air. In U.S. Pat. No. 6,053,870, small holes from the notch extend into the lumen of the needle and supply air to the notch to enhance the reflectivity. This works very well in some applications, but is problematic in others especially if the lumen of the needle is used to inject or aspirate fluids through the tip of the needle. The holes in the sidewall limit the amount of suction one can apply to the lumen and needle tip by aspirating air or other material through the side holes. In the case of injecting fluids, the fluids may exit the holes in the base of the notches rather than the tip of the needle causing the fluid to be deposited at least partially at a site other than the intended one. Hence, one embodiment of the needle of the current invention is to provide a shape, configuration, or treatment, including the filling of the notch with a substance that comprises air bubbles or other reflective material, that will enhance the retention of these small quantities of air within the notch and enhance reflectivity without having the base of the notch extend into the lumen as in the '870 patent above. Another technique to prevent the entrained air or other reflective material from being displaced from the notches is to create small cavities in the sides or floor of the notches that more or less protect the entrapped air from being displaced. Overhanging edges of the notches also would create small reservoirs where the air or other reflective materials could reside without being displaced. Other methods will be described below.

While the reflectivity will largely a result of reflections from a face of the notch, whether that face be at an acute, obtuse, or right angle to the axis of the needle shaft, the features described herein will enhance the visibility by ultrasound by providing additional reflective surface within the notch that will directly reflect the ultrasound beam and provide a nidus for attachment of small amounts of air to reflect the ultrasound beam. These additional features will allow visualization of the needle even at the steepest of angles.

The depth of the notch is also important as is the shape. Both the depth and the shape of the notch will affect the retention of small amounts of air to enhance the reflectivity. Other features, aspects and advantages of the present invention can be seen on review of the drawings, the detailed description and the claims which follow.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

In some examples the medical instrument, and in particular a needle, will provide enhanced imaging in a wide range of orientations between the axis of the needle and the ultrasonic echo sensor.

According to some examples of the needle, it is possible to provide this enhanced imaging in a design that is simple and inexpensive to manufacture and relatively simple to operate.

The advantages achieved by various examples of a needle made according to the invention are important in order to assure maximum usage of the invention in a large number and a wide variety of applications where an ultrasonically identified needle is important.

Examples of needles made according to the invention can create no additional risk of trauma to tissue. According to some examples, the needle has enhanced imaging characteristics but also maintains its function to deliver a variety of energies without compromising the shape, intensity, or any other parameter of the energy field.

There are inevitable operational trade-offs in the choice of different needle design features to achieve the above interrelated operational characteristics.

Accordingly, a surgical needle made according to the invention provides an enhanced ultrasonic visibility while also achieving one or more the following characteristics: low cost, simple structure, high degree of safety, a high degree of uniform energy deposition within the tissues, and the avoidance of complicated procedures or new techniques with which medical personnel are not familiar.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

Figure 1:
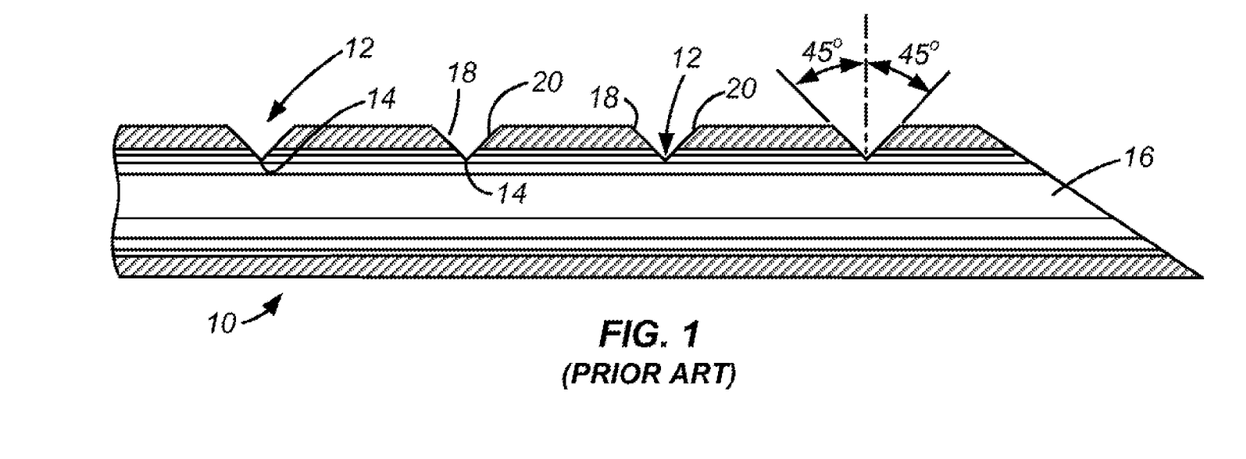
FIG. 1 is a longitudinal sectional view of a prior art device showing a particular notch arrangement at the distal portion of a needle.
Figure 2:
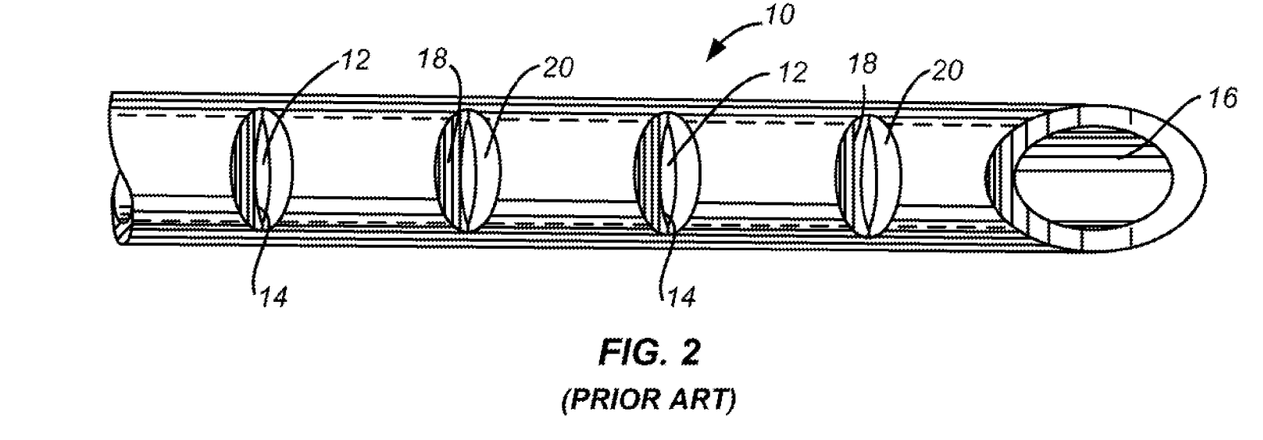
FIG. 2 is a top view of a prior art device showing notches in the sidewall of the needle.

FIGS. 1 and 2 disclose a prior art surgical needle 10. A series of notches 14 near the distal end of the needle extend around substantially less than half the circumference of the needle. Each notch 14 is cut deep enough so that over a small distance, there is an opening 12 which provides communication between the lumen 16 of the needle and the zone defined by the notch, however in some embodiments there is no communication with the lumen.

The notch 14 is cut into the sidewall. The two wall faces 18, 20 provide a relatively significant area to reflect incidence of ultrasonic energy and thus create an ultrasonic echo that can be received over a substantial area. The reflectivity of the faces is enhanced by the air that is siphoned from the lumen and into the notches when the needle is advanced through the tissue. As the needle is advanced the tissue attaches to small air bubbles and displaces the air from the notches and the air is spread along the shaft of the needle, enhancing the shaft. The air in the lumen is conveyed through the small holes at the base of the notches a re-fill the notches with air which rather dramatically enhances the reflectivity of the notches.

However, in the case in which the notch does not communicate with the lumen containing air, or in which the lumen contains fluid, the air initially within the notches may easily be displaced out of the notches rendering the notches not as reflective. The initial reflectivity enhancement provided by the air is lessened as the air initially present within the notches is removed by manipulating the needle within the tissue. This may necessitate removing the needle, washing it off to clean out the notches, removing the water from the notches by tapping the needle repeatedly, and then replacing the needle with air again present within the notches. This series of maneuvers is problematic and one major object of the present invention is to provide a means to retain the air bubbles within reflective notches in the needle sidewall so that the needle is visible by ultrasound after multiple passes and maneuvers within tissue and overcome the limitations of the prior art device.

One method of solving the above problem would be to form the notches with a right angle or obtuse angle that would tend to retain the small amounts of air within the notches as the needle is passed through the tissue. These angles and steep acute angles will retain more air than more shallow acute angles and cause the needle to be more visible under ultrasound. The depth of the notches may also contribute to retention of air, as the deeper the notch, the more likely small amounts of air will be retained within the notches, and the more likely the needle will be more visible by ultrasound.

The inventor has conducted experiments that confirm the above. Needles with notches comprising steep angles, either right, acute, or obtuse angles were evaluated in a turkey breast model utilizing standard ultrasound techniques, and all were very visible by ultrasound. Subsequently the turkey breast was immersed and covered in a water bath, the needles were agitated within the water bath to remove any air bubbles within the needle notches and then placed into the turkey breast while still under water. This latter maneuver prevented any air contact with the needle notches before inserting them into the turkey breast. The ultrasound transducer was then also immersed and scanning was performed with the needle, the turkey breast, and the ultrasound transducer all under water. The needles and the needle notches were much less visible than during the standard above water assessment. This indicates, if not proves, that much of the enhanced reflectivity is due not to the angles of the face of the notch but to the presence of small amounts of air within the notches of the needles.

Maneuvers, methods, and technology to enhance the reflectivity of the needles by ultrasound hence should include means to enhance the presence and retention of small amounts of air within the notches. Some of these means are discussed subsequently. Others will be anticipated by those skilled in the art that read this description, but are intended to be included here within.

Figure 3:
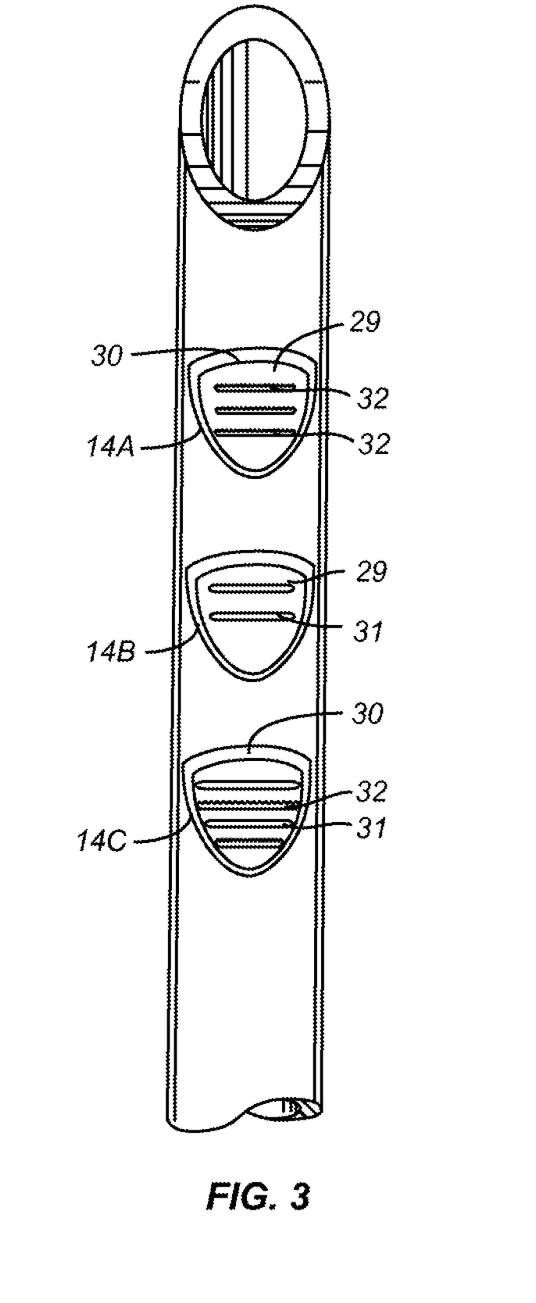
FIG. 3 is a plan view of a needle with three notches with indentations and ridges in the bottom of the notches.
Figure 8:
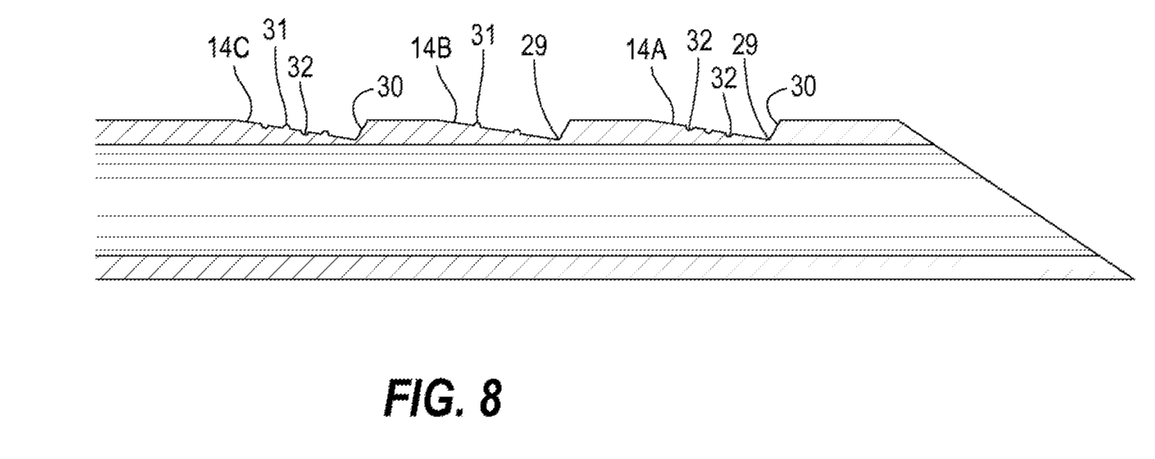
FIG. 8 is a longitudinal sectional view of the needle from FIG. 3.

FIG. 3 is a plan view of a needle and demonstrates notches 14A, 14B, and 14C with a base 29 that comprises small transverse indentations 32 and ridges 31 that will add additional surfaces of reflectivity and also retain small bubbles of air (not shown) for reflectivity enhancement. Sound will be reflected from the transverse face 30, but the additional indentations 32 and ridges 31 will enhance this reflectivity. The notch 14A comprises only indentations 32. The notch 14B comprises only ridges 31, and the notch 14C comprises both ridges 31 and indentations 32. These are oriented more or less transversely but may be oriented in other directions. FIG. 8 is a longitudinal sectional view of the needle from FIG. 3. The ridges 31 and indentations 32 are illustrated in FIG. 8 as having a curved, smooth surface however in other embodiments the ridges 31 and indentations 32 can be straight, roughened, parabolic, trapezoidal, or any other shape that forms a raised or indented surface in transverse face 30 and the base 29. While the transverse face 30 will reflect sound, the additional reflectors within the notches will enhance sound reflectivity. The ridges 31 or indentations 32 may also be present in the sidewalls or face of the notch, and may or may not be oriented more or less perpendicular to the expected incident ultrasound waves.

Figure 4:
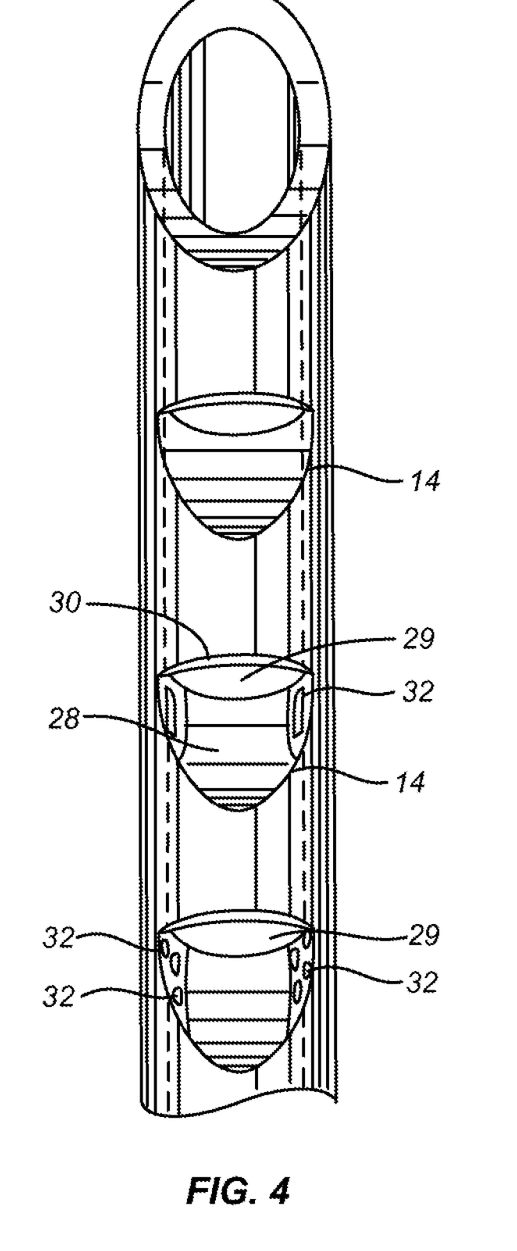
FIG. 4 is a needle with indentations in the sidewalls of the notches.

FIG. 4 demonstrates a needle 10 with a notch 14 with indentations 32 in the sidewalls of the notch 14 that provide a reservoir for bubbles of air. These sidewall indentations 32 may provide additional reflectivity, but may just serve to resupply the notch 14 with reflective air bubbles after the needle 10 passes through tissue and some of the initial air within the notches 14 is removed by the sliding action of the needle. Similarly, the indentations 32 may be placed in the floor 28 of the notch 14 (not shown.)

Figure 5:
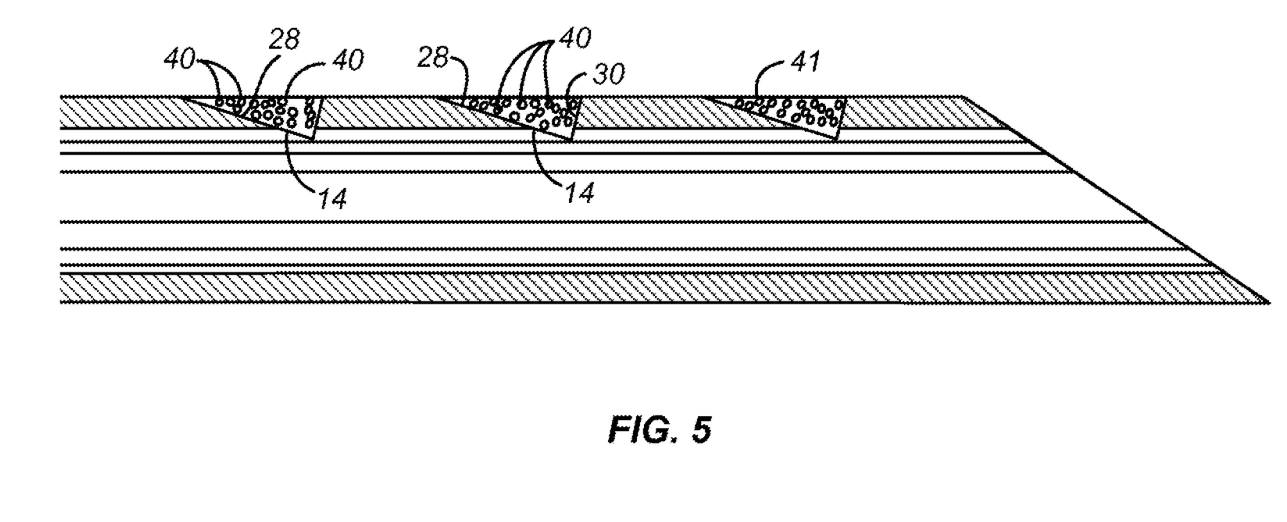
FIG. 5 is a longitudinal sectional view of the needle of the current invention with notches filled with a substance comprising small air bubbles.

FIG. 5 demonstrates a needle 10 with a notch 14 that is filled with a substance 41 that contains air bubbles 40 suspended within the substance 41. While the face of the notch 30 will provide reflectivity, these suspended air bubbles 40 will provide the reflectivity enhancement so that the needle 10 will be visible even when the shaft of the needle is at very steep angles relative to the ultrasound beam. Coatings of needles with reflective surfaces are commercially available, but tend only to enhance a needle that is not very reflective The coatings are usually comprised of a polymer, but may be any of several substances and may contain small spheres of a reflective material. The additive effect of the transverse reflective face 30 and the reflective air bubbles 40 within the notch 14 will reflect sound waves much better than a coating over a smooth needle. The coated needles also tend not to slide through tissue with ease as the coatings provide friction with the tissue that makes advancement and placement of the needle problematic. This design overcomes those problems by placing the reflective substance 41 or the reflective air bubbles 40 within the substance 41 within the notches and not on the surface of the shaft of the needle.

Figure 6:
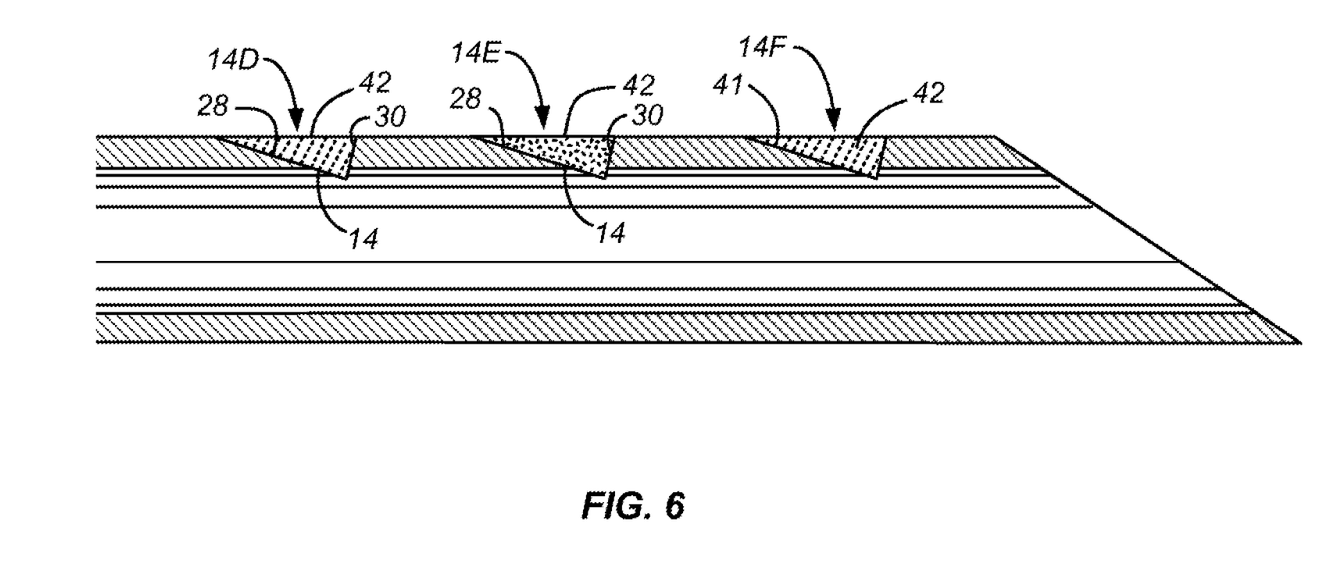
FIG. 6 is a longitudinal sectional view of the needle of the current invention with the notches filled with a substance comprising reflective particles. Alternatively, the substance may be reflective without the particles being present. Additionally, a reflective substance with reflective particles may at least partially fill the notch.

FIG. 6 demonstrates a needle 10 with a notch 14 which is filled with a substance 41 that comprises other reflective materials 42. This may comprise particles of a reflective material 42 suspended in a substance 41 that fills the notch 14 or the substance 41 that fills the notch 14 may actually be the reflective material with different ultrasound impedance properties than tissue and the needle shaft. Additionally, in the case of reflective particles 42 within a substance 41, the particles 42 may be randomly oriented as in the case of notch 14E, or oriented in a consistent manner as in notch 14D. This may be accomplished by applying a magnetic field, for example, or some other means to the notch during the process of filling the notch 14D. Aligning the particles so they are more or less parallel with the transverse face 30 may enhance the reflectivity more than any other orientation. Notch 14F demonstrates different sized particles 42. These are just examples of different configurations and orientations. This configuration solves the problems caused by coating the needle shaft discussed in the preceding paragraph. The substance which fills the notch may be one of many different substances, and ideally the outer surface of the substance filling the notch will be continuous with the outer surface of the needle shaft creating a smooth transition from needle shaft to notch to needle shaft. This will essentially restore the cylindrical surface to the needle shaft by filling the notch and allow it to traverse tissue more easily. As well, there would be no concern that the reflective material would be displaced from the notch by the passage of the needle through tissue. Alternatively, the notch may be only partially filled with the reflective substance or substance which contains the reflective material.

In FIG. 6, the notches 14 of the needle are filled with a substance 41 that will create enhanced echoes from the notch 14, but is also of similar electrical conductivity as the needle. This substance ideally has echogenic properties as dissimilar as possible as the needle, but electrical conductivity and energy transmissive qualities as close to the metal needle as possible. This will allow the transmission and deposition of an energy field of choice in a homogeneous manner within the chosen tissue.

Figure 7:
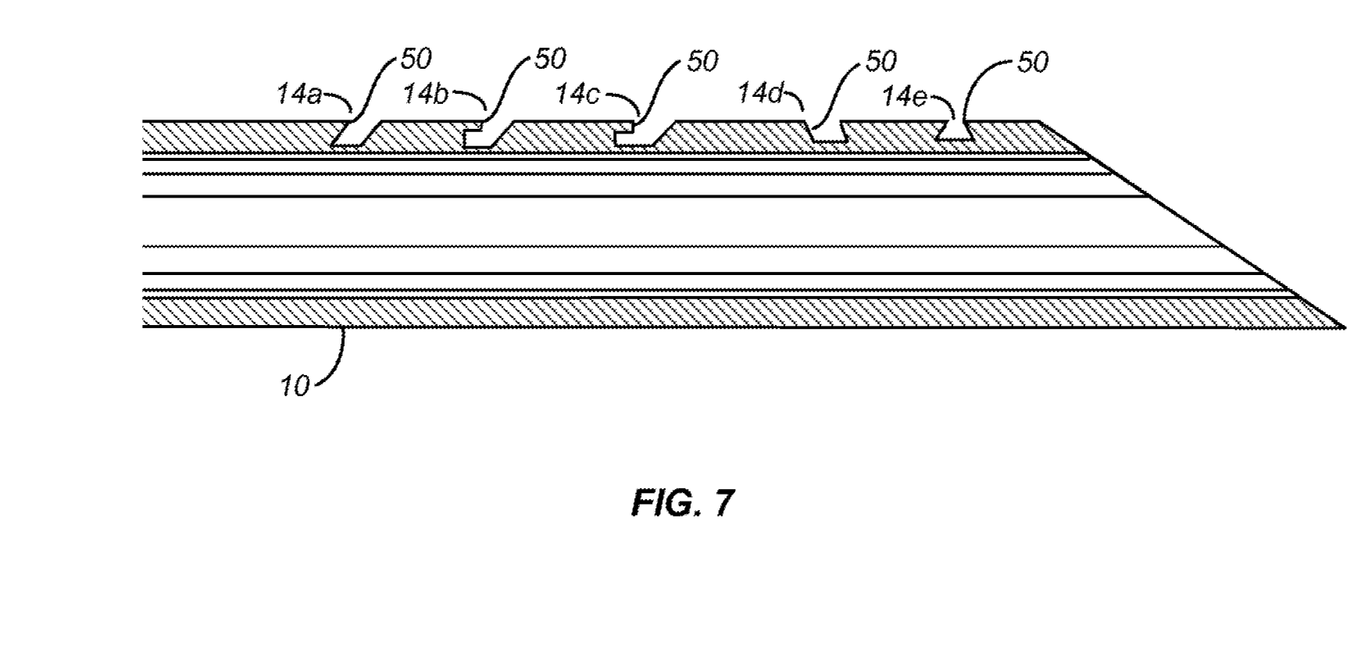
FIG. 7 is a longitudinal sectional view of a needle with notches of differing configurations that have overhanging surfaces that create cavities that harbor the air bubbles when the needle is inserted into the tissue and prevent the sliding action of the needle from dislodging the air bubbles from the notches.

FIG. 7 demonstrates a needle 10 with a notch 14 with overhanging edges 50 of the notch 14 which provide a reservoir of sorts for the air to remain in when the needle is advanced through tissue. Possible different shapes are illustrated in notches 14a through 14e but shapes and configurations are not limited to these configurations.

While not demonstrated herein, any combination of the above features may enhance reflectivity even more. For example, small indentations and ridges may be present within a notch that comprises a substance with ultrasonic reflective materials.

Although this invention has been described in connection with particular embodiments, it should be understood that there would be variations on the embodiment shown which would provide the advantage of the invention that are included in the teachings herein.

For example, reference is made throughout the specification in claims to a needle. However, it is conceivable that there may be certain situations in which some cannula other than a needle would advantageously employ the arrangement of this invention. It should be understood herein that a needle is defined to include such cannulas.

In certain incidences, it may be advantageous to utilize both the passive method of providing means to enhance the residence of air bubbles within the notches as described in the preceding paragraphs, and the active method of urging air, CO2, microspheres, contrast agent, etc., into the lumen of the device by pumping or some other means. This may be accomplished by utilizing a needle design with small holes in the base of the notches and inserting a small amount of air, CO2, microspheres, contrast agent, etc., via a bulb or some other structure attached to the device, or a small air, CO2, microspheres, contrast agent, etc., containing bladder, cartridge, or vessel in addition to using ambient air.

Further, in utilizing ultrasound guidance to locate tumors and to place probes within or adjacent to the tumors, it is necessary to locate the needle as has been described above. This can be successfully done with the current invention. However, if probes are utilized to deliver an energy field to the tumor or tissue, the notches in the needle which provide the enhanced ultrasonic visibility may cause the energy field to be non uniform with irregular areas of more or less energy. In this case, it may be advantageous to place the notches facing away from the tumor and the transducer beam so that the smooth side of the needle is facing the tumor or the tissue into which the energy is to be deposited. This can be accomplished by simply rotating the needle 180 degrees from the visualization position to the "treatment" position.

Alternatively to preserve a uniform energy field, a substance may be placed within the notches that provides a tissue interface within the notches to reflect the ultrasound beam, but does not interfere with the energy field deposition. Any air within the notches would affect the uniformity of the energy field more than most other substances, and filling the notches with a substance that would displace the air while providing for enhanced reflectivity of the ultrasound beam and delivering a uniform field of energy to the field would be optimal. Since the reflectivity is a product of the angle of the notches within the needle and the dissimilar interface between metal of the needle and the substance within the notches, the substance that fills the notches should be as much unlike the metal needle as possible. A gel may fill these requirements, as may any one of a number of substance including hydrogels, polymers, synthetics, hydrophilic plastics, and the like.

Moreover the electrical conductivity properties of the substance that fills the notches should be as much like the metal needle or probe as possible so as to deliver the energy field in a manner as close to the metal needle or probe as possible. Hence, the substance within the notches may contain certain ions or chemicals that enhance electrical conductivity or energy transference.

In another embodiment, an inner stylet may conduct the energy through the outer ultrasound visible sheath of the needle and the energy deposited by the inner stylet. This would solve the problems of the non uniform energy field caused by the notches, but may cause the overall size of the needle to be larger to accommodate the inner stylet and the outer sheath.

In still another embodiment, it may be advantageous to insulate the outer surface of the needle with a non-conductive substance and transmit the radiofrequency current, electrical current, or other energy along the shaft of the needle to a location not covered by the insulating material. This would allow the energy to be administered only at the tip of the needle, or at some other predetermined location along the needle shaft that did not have the insulating material. In a preferred embodiment, the insulating material may also comprise reflective properties so that the insulating material also aids in reflectivity. In still another embodiment, a reflective material is deposited into the notches to enhance ultrasound visibility and the insulator material is applied over the wall of the needle also covering the notches containing the aforementioned reflective material.

One particular use for the device of the current invention or any other needle for that matter is to utilize it in renal denervation to control hypertension. It has been shown that by delivering radiofrequency pulses or other energy sources to the renal arteries via a catheter in the renal arteries, that the radiofrequency (RF) pulses or other energy damage the nerve fibers that are located just outside the renal artery. The damage is enough to diminish the nervous system stimulation to the kidneys and thereby diminish the nervous, hormonal and humoral pathways that have caused the hypertension. This system, termed "renal denervation," is effective, but requires an invasive catheterization of the arterial system. Another method of renal denervation involves imaging the renal artery with ultrasound, placing a cannula or the sort adjacent to the renal artery and delivering RF or other energy to the periarteial space containing the nerve fibers through the needle. The process is then repeated on the contralateral side. This has not been described before and is an invention in its own right.

The device of the current invention may be used to deliver radiofrequency or other pulses to the soft tissue and nerves adjacent to the renal artery by using ultrasound guidance. The means for retaining ultrasonic reflective material within the notches or indentations will dramatically improve the ease at which the needle can be guided into appropriate position for the delivery of the energy. The placement of the needle needs to be precise and the reflectivity of needles without this feature will be problematic in that they will not be easily visualized.

The present invention may be a surgical needle visible to ultrasound comprising: a generally cylindrical, commonly tubular structure and having an axis, said structure having at least one notch, said notch having a first face that reflects ultrasound and a means for retaining ultrasonic reflective material to enhance the reflectivity of the ultrasound. The notch may be located only on one side of the needle. The said notch may comprise indentations which enhance ultrasound reflectivity.

The tubular structure is solid or the structure comprises a sidewall containing a lumen. The notch may comprise a substance with substantially different echogenicity than the needle. The notch comprises a substance with substantially the similar energy conductivity properties as the needle. The surgical needle of the current invention may be a tubular structure and having an axis, said structure having at least one notch, said notch having a first face that reflects ultrasound, and said notch comprising indentations within the floor or sidewall of said notch. It may comprise a means for entraining small air bubbles within said indentations. There may be reflective material in the notch comprised of one of air or other reflective material. The notch of the needle may be comprised of a face of one of either an acute, right, or obtuse angle. It may have an indentation whose depth replaces a substantial portion of the needle sidewall. The notch may have either indentations or ridges or both to entrail air bubbles.

Energy may be delivered through the needle of the current invention and deposited into tissue. The energy may be radiofrequency energy, irreversible electroporation, radiation, focal ultrasound, heat, cryotherapy, or other energy.

The present invention may be utilized in method of depositing energy into tissue wherein the tissue to be treated is localized by the echogenic enhancing properties of the device, and energy is delivered through the device and the device removed. Also a method of depositing energy into tissue utilizing the device of the current invention wherein the tissue to be treated is localized by the echogenic enhancement properties of the device, the device is rotated 180 degrees, and the energy is delivered through the device and the device removed. A method of renal denervation comprising placing a needle or cannula under ultrasound guidance adjacent to the renal artery, delivering an energy sufficient to damage the nerves adjacent to the renal artery, and removing the needle is described herein.

While the above descriptions have been directed toward enhancing ultrasound reflectivity while depositing energy fields to treat tumors, the above devices and methods may be utilized to deposit any type of energy for other applications including but not limited to nerve stimulation, nerve blocks, coagulation, ablation, treatment of vascular lesions, thrombolysis, prevention of restenosis, excitation of microspheres, and the like.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

The invention claimed is:

1. A surgical needle visible to ultrasound, comprising:
a tubular structure having an outer surface that spans circumferentially around a longitudinal axis of the tubular structure, the tubular structure having a notch, the notch having a plurality of faces, wherein the notch has a projection that extends from the outer surface to cover a portion of at least one of the plurality of faces to form a reservoir configured to retain an ultrasonic reflective material.

2. The surgical needle of claim 1, wherein the projection is arranged substantially parallel to the longitudinal axis.

3. The surgical needle of claim 1, wherein the projection includes at least two projection faces that are configured to retain the ultrasonic reflective material.

4. The surgical needle of claim 3, wherein a first projection face and a second projection face of the at least two projection faces form an acute angle with the outer surface of the surgical needle.

5. The surgical needle of claim 1, wherein the projection includes an overhanging edge.

6. The surgical needle of claim 1, wherein a face of the plurality of faces has an overhanging edge, wherein the face and the overhanging edge are configured to retain the ultrasonic reflective material.

7. The surgical needle of claim 1, wherein the plurality of faces includes a face that forms an acute angle with another face of the plurality of faces.

8. The surgical needle of claim 1, wherein the plurality of faces includes a face that forms an obtuse angle with another face of the plurality of faces.

9. A surgical needle visible to ultrasound, comprising:
a tubular structure having an outer surface that spans circumferentially around a longitudinal axis of the tubular structure, the tubular structure having a notch, the notch having a plurality of faces, wherein a first face of the plurality of faces is configured and arranged to overhang a portion of a second face of the plurality of faces to retain an ultrasonic reflective material between the first face and the second face.

10. The surgical needle of claim 9, wherein the first face forms an acute angle with the second face.

11. The surgical needle of claim 9, wherein the first face includes an overhanging edge.

12. The surgical needle of claim 9, wherein the notch includes a third face of the plurality of faces, the second face arranged to contact the third face.

13. The surgical needle of claim 12, wherein the second face and the third face form an acute angle there between, the third face includes a second overhanging edge that extends over a portion of the second face.

14. The surgical needle of claim 12, wherein the second face and the third face form an obtuse angle there between.

\* \* \* \* \*